(12) United States Patent
Coelho

(10) Patent No.: US 8,727,980 B2
(45) Date of Patent: May 20, 2014

(54) UMBILICAL PROBE SYSTEM

(75) Inventor: Peter Coelho, Hollister, CA (US)

(73) Assignee: Medicalcue, Inc., Mountain View, CA (US)

( * ) Notice: Subject to any disclaimer, the term of this patent is extended or adjusted under 35 U.S.C. 154(b) by 409 days.

(21) Appl. No.: 13/044,943

(22) Filed: Mar. 10, 2011

(65) Prior Publication Data

US 2012/0232357 A1    Sep. 13, 2012

(51) Int. Cl.
*A61B 5/00* (2006.01)
*G06F 19/00* (2011.01)
*A61B 17/42* (2006.01)

(52) U.S. Cl.
CPC  *G06F 19/34* (2013.01); *A61B 17/42* (2013.01)
USPC ............................................. 600/301

(58) Field of Classification Search
USPC ................................. 600/300–301
See application file for complete search history.

(56) References Cited

U.S. PATENT DOCUMENTS

| | | | |
|---|---|---|---|
| 3,016,056 A | 1/1962 | Bay | |
| 3,674,032 A | 7/1972 | Minganti | |
| 4,086,917 A * | 5/1978 | Burks et al. | 600/453 |
| 4,572,181 A * | 2/1986 | Mattler | 606/174 |
| 5,370,627 A | 12/1994 | Conway | |
| 5,415,665 A | 5/1995 | Hessel et al. | |
| 5,440,295 A | 8/1995 | Ciecwisz et al. | |
| 5,667,516 A * | 9/1997 | Allen | 606/120 |
| 5,676,672 A * | 10/1997 | Watson et al. | 606/120 |
| 5,695,740 A * | 12/1997 | Porter | 424/9.52 |
| 5,749,831 A | 5/1998 | Baker | |
| 5,779,631 A | 7/1998 | Chance | |
| 6,155,976 A * | 12/2000 | Sackner et al. | 600/300 |
| 6,254,537 B1 * | 7/2001 | Nguyen | 600/300 |
| 6,425,861 B1 * | 7/2002 | Haberland et al. | 600/300 |
| 6,453,186 B1 | 9/2002 | Lovejoy et al. | |
| 6,648,820 B1 * | 11/2003 | Sarel | 600/300 |
| 7,291,109 B1 | 11/2007 | Sarvazyan | |
| 7,321,862 B2 | 1/2008 | Rosenfeld et al. | |
| 7,411,509 B2 | 8/2008 | Rosenfeld et al. | |
| 7,433,827 B2 | 10/2008 | Rosenfeld et al. | |

(Continued)

FOREIGN PATENT DOCUMENTS

| | | |
|---|---|---|
| CN | 1228290 A | 9/1999 |
| CN | 200977155 Y | 11/2007 |

OTHER PUBLICATIONS

Kattwinkey, J. et al., "Special Report Neonatal Resuscitation: 2010 American Heart Association Guidelines for Cardiopulmonary Resuscitation and Emergency Cardiovascuair Care," *Pediatrics*, 16 pages, published online at http://www.pediatrics.org on Oct. 18, 2010.

(Continued)

*Primary Examiner* — William Thomson
*Assistant Examiner* — Bobby Soriano
(74) *Attorney, Agent, or Firm* — Wilson Sonsini Goodrich & Rosati

(57) ABSTRACT

An umbilical probe sensing system is described which includes an automated system for accurately obtaining physiological information from an infant in real time. The system may also automatically guide a healthcare provider with a recommended course of treatment for infant resuscitation based on the detected and monitored physiological data. Moreover, the automated system may also provide a real time record of the infant's physiological parameters and resuscitation treatment performed by a healthcare team.

21 Claims, 9 Drawing Sheets

(56) References Cited

U.S. PATENT DOCUMENTS

| | | | |
|---|---|---|---|
| 7,454,359 B2 | 11/2008 | Rosenfeld et al. | |
| 7,539,533 B2 | 5/2009 | Tran | |
| 7,650,291 B2 | 1/2010 | Rosenfeld et al. | |
| 7,733,224 B2 | 6/2010 | Tran | |
| 7,875,037 B2* | 1/2011 | Lemke et al. | 606/120 |
| 2002/0044059 A1 | 4/2002 | Reeder et al. | |
| 2004/0073094 A1* | 4/2004 | Baker | 600/300 |
| 2004/0103001 A1 | 5/2004 | Mazar et al. | |
| 2006/0258924 A1 | 11/2006 | Al-Ali et al. | |
| 2006/0281983 A1 | 12/2006 | Al-Ali et al. | |
| 2007/0276273 A1 | 11/2007 | Watson, Jr. | |
| 2008/0071155 A1 | 3/2008 | Kiani | |
| 2009/0024043 A1 | 1/2009 | Macleod et al. | |
| 2009/0030318 A1 | 1/2009 | Lemke et al. | |
| 2009/0148822 A1* | 6/2009 | Eggert et al. | 434/271 |
| 2009/0192364 A1* | 7/2009 | Voto et al. | 600/301 |
| 2009/0216564 A1* | 8/2009 | Rosenfeld | 705/3 |
| 2009/0240098 A1* | 9/2009 | Ten Eyck et al. | 600/22 |
| 2009/0287120 A1* | 11/2009 | Ferren et al. | 600/587 |
| 2009/0318779 A1* | 12/2009 | Tran | 600/301 |
| 2010/0030122 A1* | 2/2010 | Gaspard | 601/136 |
| 2010/0030145 A1 | 2/2010 | Ghodsian et al. | |
| 2010/0049221 A1* | 2/2010 | Baker et al. | 606/151 |
| 2010/0130500 A1 | 5/2010 | Kakkis | |
| 2010/0227303 A1* | 9/2010 | Deering | 434/273 |
| 2010/0268108 A1* | 10/2010 | Firminger et al. | 600/544 |
| 2010/0318025 A1* | 12/2010 | John | 604/84 |
| 2011/0098730 A1* | 4/2011 | Kelleher | 606/151 |
| 2011/0190611 A1 | 8/2011 | Rabi | |
| 2012/0116174 A1* | 5/2012 | Tighe et al. | 600/249 |
| 2012/0232356 A1 | 9/2012 | Coelho | |
| 2012/0232358 A1 | 9/2012 | Coelho | |

OTHER PUBLICATIONS

Ramirez, R. et al., "Oxygen Management of the Very Low Birth Weight Infant," *RT Magazine*, 4 pages, published online at http://www.rtmagazine.com/issues/articles/2010-02_03.asp on Feb. 3, 2010.

Schachinger, H., "Non-invasive monitoring of the cardiopulmonary status of newborn infants immediately following birth," *Klin Padiatr*, vol. 2: pp. 161-163, Abstract only [article in German], Mar.-Apr. 1985.

International search report and written opinion dated Dec. 24, 2012 for PCT/US2012/058341.

Office action dated Feb. 27, 2013 for U.S. Appl. No. 13/044,858.

Office action dated Feb. 27, 2013 for U.S. Appl. No. 13/249,743.

* cited by examiner

80 ↘  82 ↓  86 ↓  88 ↘

| Heart Rate | Measurements | Documentation and timer buttons |
|---|---|---|
| 130 O2 Saturation 98% Weight 3.5 kg Time Elapsed 90 secs | Blade= ET Tube size= ET Tube length= Narcan= Epinephrine Et= Epinephrine IV= Bolus Bicarb= UVC size= OG tube= | (see table below) |

| | |
|---|---|
| Stop | Start |
| Active Respirations | Weigh |
| Blow-by | CPAP |
| PPV | Compressions |
| Intubation | Narcan |
| Epinephrine | Bicarb |
| Fluid Bolus | Orogastric Tube |
| UAC | UVC |
| Peripheral IV line | Blood glucose |
| APGAR | Data Input |
| Score | Qwerty |
| Send Button | |

Prompts-

Dry, position, suction

Positive Pressure Ventilations

Chest Compressions

Intubation

Lines- OG, UVC, UAC, PIV

Fluids-D10W, Bicarb

Oxygen Mixture

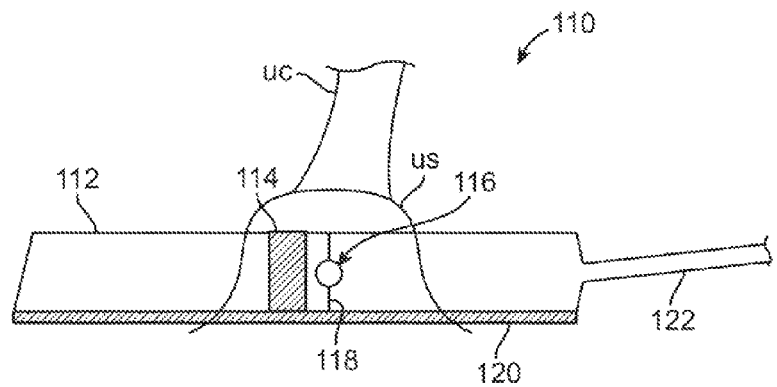
FIG. 7A
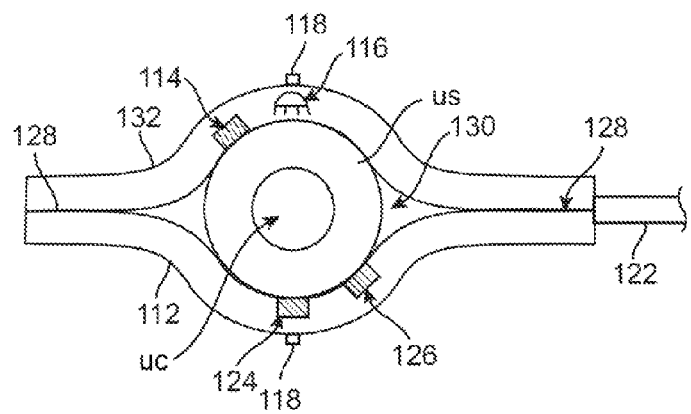
FIG. 7B
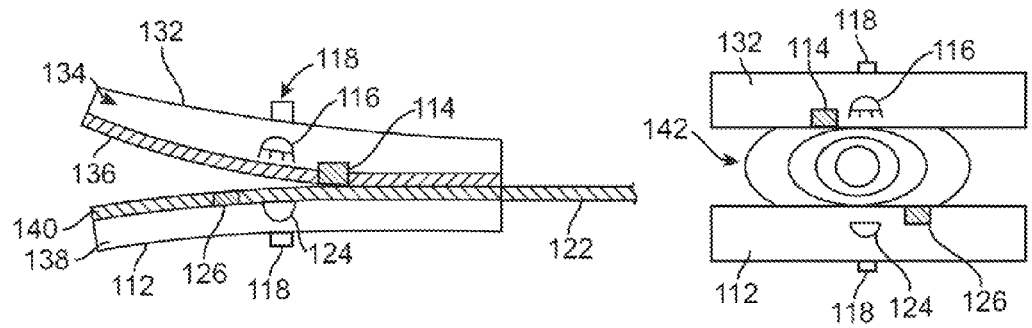
FIG. 8A
FIG. 8B

UMBILICAL PROBE SYSTEM

FIELD OF THE INVENTION

The present invention relates to methods and apparatus for sensing one or more physiological parameters from a newly born infant. More particularly, the present invention relates to methods and apparatus for sensing one or more physiological parameters from a newly born infant and guiding a treatment for the infant utilizing the sensed physiological parameters.

BACKGROUND OF THE INVENTION

With 4.2 million babies born yearly in the United States alone, 10% of all these newborns require some assistance to initiate breathing at birth and 1% of all these newborns require extensive resuscitation to survive. To assist medical care providers in the resuscitation of these infants, the American Academy of Pediatrics (AAP) and the American Heart Association (AHA) have developed a standardized sequential system, commonly known as the Neonatal Resuscitation Program (NRP) for evaluating a newborn and administering resuscitative measures which may include the application of pressurized oxygen, chest compressions, medications and endotracheal intubation to prevent asphyxiation, brain injury and death following birth.

In order to participate in neonatal resuscitation, a practitioner is typically enrolled in a certified NRP class which requires the memorization of clinical algorithms, passage of a written exam, and demonstration of clinical proficiency in neonatal resuscitation procedures. They are then granted a 2 year certificate attesting to their competency in performing neonatal resuscitation. NRP competency has become the standard of care for granting privileges to physicians to care for infants in hospital nurseries throughout the U.S.

Neonatal resuscitation is a complex system of procedures, decision making and medication administration based on a memorized algorithm with time constraints performed under pressure while a newborn is dying. The infant's life depends on the practitioner memorizing this algorithm, guessing the weight of an infant, counting the infant's heart rate and incorporating the appropriate procedures, medication administration and calculating appropriate device sizes and medication dosages based on approximation of the infant's weight. Presently, there are no assistive devices to measure the infant's weight, measure heart rate, calculate appropriate device sizes, calculate appropriate medication dosages, pace procedures, time procedures and medication administration and simultaneously record and create a document that represents the resuscitative effort for the medical record. In addition, the current medical culture does not provide a system to gather and analyze outcome data from present resuscitation methods for refinement.

After a baby is born (either vaginally or by cesarean section), the umbilical cord is clamped with a plastic clip and cut by a physician and handed off to another physician or nurse to be laid on a neonatal warmer for evaluation. The clamp is permanent and non-adjustable and typically crushes the tissue of the umbilical cord and is placed randomly along the cord. A theoretical clock starts upon arrival of the baby to the warmer. Within the first 30 seconds, the baby is dried, stimulated, positioned and airways are cleared of secretions with a suction device. The baby is typically evaluated for resuscitation based on three variables: breathing efficiency, heart rate, and color. However, the time to the first data acquisition of a distressed infant can range anywhere from thirty seconds to a few minutes. Moreover, the methodology for obtaining the physiological information from the infant typically involves obtaining the heart rate by squeezing the umbilical cord between the thumb and index finger and counting pulsations, using a stethoscope to listen to the lungs and an estimate or guess of neonatal weight. Such measurements are open to human error and subjectivity. If the baby is actively breathing, heart rate is greater than 100 beats per minute (BPM) and central color is pink, the baby is observed and given an evaluative score called the Apgar score at an interval of 1 minute, 5 minutes, and 10 minutes. The infant is then returned to the mother.

On the other hand, if the baby has either poor or no respiratory effort, a heart rate less than 100 BPM or central cyanosis, a time based algorithm is enacted. Each 30 seconds the infant is re-evaluated utilizing these three criteria and a new set of procedures are performed and/or medications are administered. The baby's weight is estimated and appropriate sized devices and medication dosages are mentally calculated based on this weight estimate. Also, the physiologic data is obtained only intermittently with about thirty seconds between data points and the determination of the data is also time-consuming.

Currently the health care provider sets up the neonatal warmer equipment, resuscitation equipment, equipment settings and medications by memory usually without an assistive device. They then simultaneously evaluate the baby's respiratory effort, color, heart rate, and estimate weight and time elapsed without assistive devices.

Neonatal heart rate is typically obtained by a health care practitioner after birth by squeezing the thumb and index against the umbilical cord and counting the number of pulsations over a 6 to 30 second period. Heart rate evaluation is subjective and biased by psychological pressure placed on the practitioner to verbally state a heart rate to the team under time constraints in hopes to rapidly apply the NRP algorithm. Accuracy can be compromised by a desire for expediency. Heart rate data is manually intensive requiring one practitioner to stop all other duties and procedures while assessing heart rate.

Presently, several types of physiological assessments for infants are either not performed or are performed after several minutes of delay. For example, electrocardiogram (ECG) rhythm analysis is not performed because of the time it takes to place the leads on the infant and the poor adherence properties of adhesives on wet, greasy skin. Similarly, pulse oximetry is not universally used by many institutions within the first few minutes of resuscitation. Moreover, standards for normal oximetry values within the first minutes of life are not yet universally agreed upon and placement sites for pulse oximetry sensors have not yet been standardized. Additionally, pulse oximetry sensor signals are typically not reliable within the first 75 seconds after placement and ambient light also degrades oximeter signals. While the limbs and digits of the infant are commonly used for sensor sites, infant movement of the limbs and digits creates movement artifact leading to inaccurate measurements.

Neonatal temperature measurement is usually performed five to ten minutes after delivery. An adhesive-based probe is placed on the chest of the neonate, which has very poor adherence quality and poor signal reliability. Another measurement which is typically not routinely performed on neonates includes measurement of $CO_2$ saturation.

Thus, the assessment and/or consideration of physiologic data is intermittent and not continuous. There are spot checks for physiologic data collection during resuscitation that interferes with the timing and flow of procedures and medication administration. However, manual physiologic data assessment creates unnecessary manpower, time and intellectual demands. The data is subjective and usually obtained under moments of stress with poor reproducibility and high noise to signal ratio. The type and quality of data that is acquired is variable from practitioner to practitioner and institution to institution. Moreover, adding to the inaccuracy of the information are the forms of data acquisition, e.g., the manual use of fingers to count pulsations in the umbilical cord or using variable qualities of stethoscopes by practitioners of variable skill levels to listen for heart tones and respiration rate.

Accordingly, medical records are presently subjective and most neonatal resuscitation records are retrospective and not recorded in real-time. When there is enough staffing to perform neonatal resuscitation, one provider is obligated as the event recorder. Tool size and medical device placement is dependent on a guess of neonatal weight and age of gestation. Procedure timing is also based on a best guess estimation of size of infant, intermittent spot physiologic data that is subjective and best estimate of time elapsed. Moreover, the time line is variable as many institutions use a viewable clock or timer. Also, the start time of the timer is also variable and is typically interrupted by the demands on practitioners to gather manually obtained physiologic data.

Medical dosages are mentally calculated during the resuscitation based on best guess of weight and correlated with best guess of time elapsed for timing of medication dosages. Oxygen blend settings are subject to the preference of the practitioner present or the institution that the resuscitation is performed in, not on specific real time neonatal physiologic data in congruence with standardized settings based on random control trial outcome data. Consequently, consistent data acquisition is given secondary priority to performing procedures on the infant.

With respect to the clamping of the umbilical cord or umbilical stump of the infant, the umbilical cord is typically clamped closed at an arbitrary location along the cord using a clothes pin-type clamp such as a Hollister Double-Grip Umbilical Cord Clamp™ (Hollister, Port Melbourne, Australia). The clamp provides hemostasis and the clamp position is fixed and permanent where the umbilical cord must be cut to remove the clamp. However, the clamp typically crushes the sight of clamping such that the tissue is crushed and the blood vessels within the umbilical cord are rendered nonviable and inaccessible. A new section of the cord must be severed to access intact umbilical vein and arteries. A second clamp is typically placed and locked on the umbilical cord and scissors are used to cut between the two clamps severing the umbilical cord in half to separate the infant from the placenta.

Frequently, the permanent clamp is placed on the umbilical cord adjacent to the fetal skin on the umbilical stump thus crushing the remaining portion of viable umbilical cord. The pediatrician caring for the infant needs a viable undamaged portion of the umbilical cord to gain access to the umbilical vessels with a plastic catheter in order to draw blood, administer medications, and administer fluids. Frequently, an inadequate portion of umbilical cord is left for the pediatrician to gain venous or arterial access to the infant.

Additionally, if the healthcare provider requires intravenous access to the infant, the umbilical cord stump is typically prepared by cutting off the permanent cord clamp and using two pairs of tweezers to thread a long pliable catheter into the umbilical vein. The length of the catheter insertion is usually estimated by the practitioner and the umbilical venous catheter is usually held in place by tying a ribbon around the umbilical cord crimping the umbilical cord around the umbilical vein catheter. This procedure is usually performed three to ten minutes into the resuscitation attempt and requires anywhere from five to fifteen minutes for correct placement of the catheter depending on the skill level of the practitioner. However, the umbilical vein catheter is prone to being positioned incorrectly and dislodged if when bumped.

Another difficulty in neonatal resuscitation is poor communication amongst the resuscitation team. Practitioners can have stethoscopes in their ears decreasing their ability to hear verbal communication by other practitioners. Physiologic data is announced verbally which can be easily ignored or unheard by entire resuscitation team. Communication can also be inhibited by practitioner hierarchy. If the leader of the resuscitation team is making inappropriate decisions or assessments, higher skilled practitioners with lower job titles tend to not communicate in order to avoid interpersonal conflict.

Accordingly, there exists a need for methods and devices for accurately assessing the physiological conditions of a newly born infant in real time and for facilitating the treatment of a distressed infant. Additionally, there also exists a need for methods and devices for clamping the umbilical cord while maintaining viable access to the cord and/or stump.

SUMMARY OF THE INVENTION

An automated system may be utilized for accurately obtaining physiological information from the infant in real time as well as automatically guiding the healthcare provider with a recommended course of treatment. Moreover, the automated system may also provide a real time record of the infant's physiological parameters and resuscitation treatment performed by the healthcare team.

Generally, an adjustable clamping sensor assembly may be placed by a healthcare provider, e.g., obstetrician, nurse, etc., to a portion of an neonatal infant's umbilical stump and/or umbilical cord immediately or shortly after birth. The assembly may be temporarily secured against the abdominal wall of the infant while the assembly maintains umbilical cord vessel integrity. Placement can be corrected by loosening the clamp and adjusting the position along the cord.

The sensor assembly, platform upon which the infant may be placed, as well any additional sensors may each be electrically coupled to a central processor which may be further electrically coupled to a display and/or user interface, e.g., monitor, interactive touchscreen, etc., as well as an optional user interface, e.g., keypad, keyboard, mouse, microphone, etc., for interacting with the healthcare provider.

In use, once the sensor assembly has been adjustably affixed to the umbilical stump, the processor may begin to receive physiological data detected from the infant. Alternatively, the processor may optionally begin once the infant has been placed upon the platform. The sensor assembly may provide for a focal area of data collection and may also provide a single site of data acquisition from the umbilical stump, which is a capillary rich site on the neonatal anatomy. Because the sensor assembly may be attached onto the umbilical stump by applying controlled pressure below the level of tissue injury (e.g., a pound or more of force), use of adhesives can be avoided as adhesives are prone to slip on wet or greasy neonatal skin and the signal quality and reliability are improved over sensors which are normally adhered to the infant's skin.

Data acquisition may be nearly instantaneous once the assembly has been secured along the umbilical cord stump and/or the umbilical cord. For example, physiological parameters such as heart rate, ECG waveform, oxygen saturation, weight, transcutaneous carbon dioxide level, etc., may be detected by the assembly and relayed to the processor. The computer displays the objective data on the interface for the entire team to view.

Data may be gathered objectively by the probe thereby reducing the need for multi-tasking or manually acquiring the information from the infant. Moreover, the assembly may also provide for a continuous stream of physiological information allowing for a more time sensitive evaluation of the neonatal physiologic state and which allows the practitioner to continue life-saving procedures while the system acquires the physiologic data for the provider.

With the physiological data acquired automatically and in real time, this information may be obtained objectively rather than relying on the subjective measurements prone to human error. Moreover, this information may be communicated directly to a processor which may evaluate the state of the infant and automatically calculate and guide the practitioner with an automated checklist for a recommended course of treatment based upon accepted and standard methods for infant resuscitation.

Once an infant has been placed upon a platform electrically coupled to the processor, an automated clock may be started by the processor and the interface may provide visual and/or auditory prompts based on the programmed resuscitation algorithm to guide the practitioner. The system may thus provide objective time-elapsed pacing for decisions on timing of procedures and timing of medications to be administered. In one example, the system may keep the practitioner on an appropriate time-line for endotracheal intubation and alert the practitioner when twenty seconds has been exceeded or if there is a desaturation event or bradycardiac event during intubation.

Thus, the system may provide prompts and suggestions that trigger recall of the algorithm and may also optionally allow the practitioner to confirm choices made by the provider or redirect the provider to appropriate decisions thereby decreasing decision errors. The system may further prompt the provider when an appropriate procedure should be performed and may optionally include a visual or auditory metronome to guide the technique of the provider, e.g., when providing certain procedures such as positive pressure ventilations, chest compressions, etc. The system also can record population based actual time requirements for procedures that are performed. Thus, the system may collect the physiologic data for the practitioner, perform all calculations based on an accurate objective weight, and may also provide an objective physiologic status of the infant.

Additionally, the system may also provide for real time medical record maintenance by recording and storing the continuous physiologic data with procedure timing and technique, medication timing and dosage overlay coupled to an Apgar score, physiologic score along with resultant outcome data, etc.

Moreover, the system may further allow practitioners of varying skill level to place umbilical vein catheters immediately or shortly after birth for a resuscitation procedure.

BRIEF DESCRIPTION OF THE DRAWINGS

FIG. 5 shows an example of a user interface for conveying physiological information in real time and for interfacing with the health care provider.

FIGS. 7A and 7B show side and top views of another variation of a clamping assembly.

FIGS. 8A and 8B show top views of another variation of the clamping assembly and how the assembly may accommodate a range of umbilical stump sizes.

DETAILED DESCRIPTION OF THE INVENTION

To facilitate the standardization of neonatal resuscitation amongst healthcare providers and to potentially decrease infant mortality, an automated system may be utilized for accurately obtaining physiological information from the infant (e.g., infant weight, heart rate, etc.) in a real time manner as well as automatically guiding the healthcare provider with a recommended course of treatment (e.g., suitable device sizes, medication dosages, etc.). Moreover, the automated system may also provide a real time record of the infant's physiological parameters and resuscitation treatment performed by the healthcare team.

Figure 1:
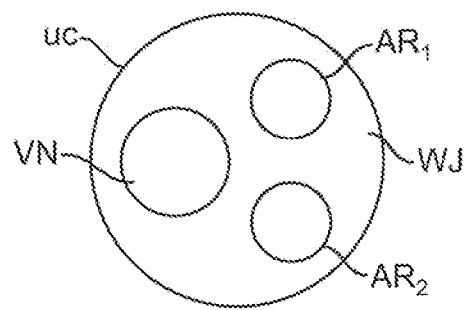
FIG. 1 shows a cross-sectional end view of an exemplary umbilical cord illustrating the blood vessels.

Normally, the umbilical cord and/or umbilical stump UC contains two umbilical arteries $AR_1$, $AR_2$ and one umbilical vein VN which are embedded within a loose, proteoglycan rich matrix known as Wharton's jelly WJ, as shown in the cross-sectional end view of FIG. 1. The clamp assembly may be designed specifically for adjustable attachment to either the umbilical cord or the umbilical stump depending upon the desired application. With the neonate's umbilical cord UC typically cut and clamped after birth, physiological information of the infant is still obtainable from the remainder of the umbilical cord and/or umbilical stump utilizing the clamp assembly described herein.

Figure 2:
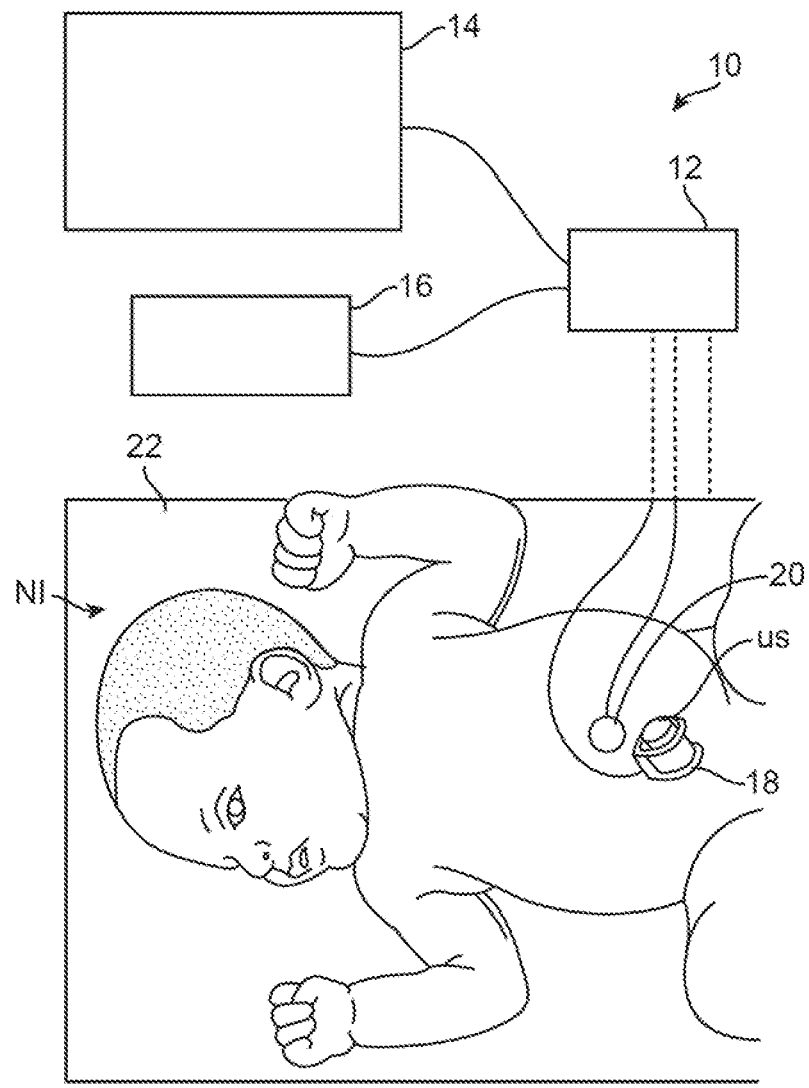
FIG. 2 shows an example, schematically, of one variation of the neonatal resuscitation system.

By utilizing this access to the umbilical cord and/or umbilical stump, the neonatal resuscitation system 10 may comprise a sensor assembly 18 which is designed for adjustable attachment to the neonate's umbilical cord and/or umbilical stump US. The sensor assembly 18 may be optionally disposable after use. As shown in the schematic view of FIG. 2, the sensor assembly 18 may be attached directly to the umbilical stump US. In addition to the sensor assembly 18, the system 10 may also comprise a platform 22 for supporting the newborn infant NI during resuscitation treatment and which may include an optional self-warming area as well as an integrated scale. An additional sensor 20, e.g., temperature probe, may also be optionally provided for temporary attachment to the infant NI, if so desired.

Each of the sensor assembly 18, platform 22, as well as optional sensor 20 may each be electrically coupled to a central processor 12 which may be further electrically coupled to a display and/or user interface 14, e.g., monitor, interactive touchscreen, etc., as well as an optional user interface 16, e.g., keypad, keyboard, mouse, microphone, etc., for interacting with the healthcare provider. The communication between the various sensors, displays and/or interface units, as well as communications with the healthcare provider may be accomplished by wired communications methods. Alternatively, the communications therebetween may be accomplished by various wireless interface protocols as well which are typically used, e.g., BLUETOOTH®, WiFi, radio frequency, microwave, cellular protocols, etc.

In use, once the sensor assembly 18 has been adjustably affixed to the umbilical stump US, the processor 12 may begin to receive physiological data detected from the infant NI. Alternatively, the processor 12 may optionally begin once the infant NI has been placed upon the platform 22. The sensor assembly 18 may provide for a focal area of data collection that is subject to low motion artifact and may also provide a single site of data acquisition from the umbilical stump US, which is a capillary rich site on the neonatal anatomy. Because of the number of different types of sensors which may be integrated compactly into the assembly 18, the number of wires that are in the resuscitation field may be decreased. Moreover, because the sensor assembly 18 may be attached onto the umbilical stump US by applying controlled pressure below the level of tissue injury, use of adhesives can be avoided as adhesives are prone to slip on wet or greasy neonatal skin and the signal quality and reliability are improved over sensors which are normally adhered to the infant's skin. Furthermore, the sensor assembly 18 may also provide a standardized, controlled, reproducible level of tissue compression to prevent tissue necrosis at sensor sites. Tissue necrosis can occur with other types of probes that are tightened by the health care workers indiscriminately on limbs and digits.

The processor 12 may be programmed with any number of resuscitation treatment algorithms which are designed to follow a particular treatment algorithm based upon the received physiological data as well as input received from the healthcare provider. In one example shown in FIG. 3, an algorithm 30 as shown in a flow chart illustrates the guidelines for neonatal resuscitation and emergency cardiovascular care as provided by the American Heart Association. Such an algorithm 30 may be programmed into the processor 12 of the neonatal resuscitation system 10 to provide, e.g., a resuscitation clock with timing, prompts for cuing the physician to appropriate interventions, pacing interventions, dosing of medications, recording of the resuscitation event, and for sending the data to a universal server, etc.

As seen, once the infant NI has been transitioned to the platform 22, the weight of the infant may be obtained automatically by the integrated scale and this weight may be transmitted to the processor 12, e.g., for automatically calculating accurate dosages of various medications to be provided to the infant NI. Platform 22 may be optionally preset to trigger various features, such as the timer, when a detected weight surpasses a threshold value, e.g., 300 gram or more. The sensor assembly 18 may be attached to the umbilical stump US either after placement upon the platform 22 or after the point of delivery, e.g., by the obstetrician once the umbilical cord has been clamped. The sensor assembly 18, as described in further detail below, may incorporate one or more sensors for detecting various physiological parameters in real time such as piezoelectric sensors for detecting heart rate, electrocardiogram (ECG) sensors, infrared pulse oximetry sensors, capnometry probe, temperature, etc. In the event that one or more temperature sensors are incorporated into the sensor assembly 18, the infant's temperature may be detected and monitored nearly instantaneously and continuously. Moreover, the infant's temperature information may be relayed to the processor 12 which may be further programmed to adjust the temperature of a warming element in the platform 22 and/or control the heat lamps above the infant.

If the infant NI is breathing or crying and shows good tone 32, the infant NI may be handed over to the mother for routine care 38. However, if the infant NI indicates respiratory distress, e.g., a detected heart rate below 100 BPM, gasping, or displays apnea 34, the system 10 may automatically detect the heart rate and oxygen saturation levels in real time from the infant NI and automatically prompt the healthcare provider or team via the interface 14 (or through another prompt) to either monitor for labored breathing 36 and/or to take further steps such as clearing the airways, prompting for positive pressure ventilation (PPV), prompting for continuous positive airway pressure (CPAP) 42, etc.

The system 10 may also prompt the healthcare provider for input based on their observations and/or judgment for providing the automated treatment options in response. Accordingly, the healthcare provider may input information into the system 10 via the interface 14 and/or optional interface 16 such that the system 10 provides the appropriate treatment option 40, e.g., PPV, pulse oximeter oxygen saturation (SpO2) monitoring, etc. Each of the physiological parameters may be monitored by the system 10 through the sensor assembly 18 (or other sensors in communication with the processor 12) and in the event that the system 10 detects a heart rate 44 falling below a specified parameter, e.g., 100 BPM, the system 10 may automatically prompt the healthcare provider to take ventilation corrective steps. In the event the heart rate detected by the system 10 falls below another specified parameter, e.g., 60 BPM, the processor 12 may be programmed to automatically prompt the healthcare provider via interface 14 to consider intubation, chest compressions, and/or coordination with PPV 48. If the detected heart rate remains below the specified heart rate parameter of, e.g., 60 BPM 50, then the processor 12 may again prompt the healthcare provider through interface 14 to consider further interventions such as an IV of epinephrine in which case the processor 12 may automatically calculate the correct dosage based upon the measured weight of the infant NI and provide the dosage to the healthcare provider. Alternatively, the healthcare provider may be prompted through interface 14 in the event that the detected heart rate rises above the specified parameter to consider ventilation corrective steps, such as intubation or other interventions.

Although certain heart rate parameters are specified herein and in the figures, they are provided merely as illustrative examples which may be programmed into the system 10. Any particular heart rate parameter may accordingly be specified and set by, e.g., the practitioner, manufacturer, AAP, AHA, etc. and the system 10 is not limited to being programmed to any particular heart rate parameter.

Figure 3:
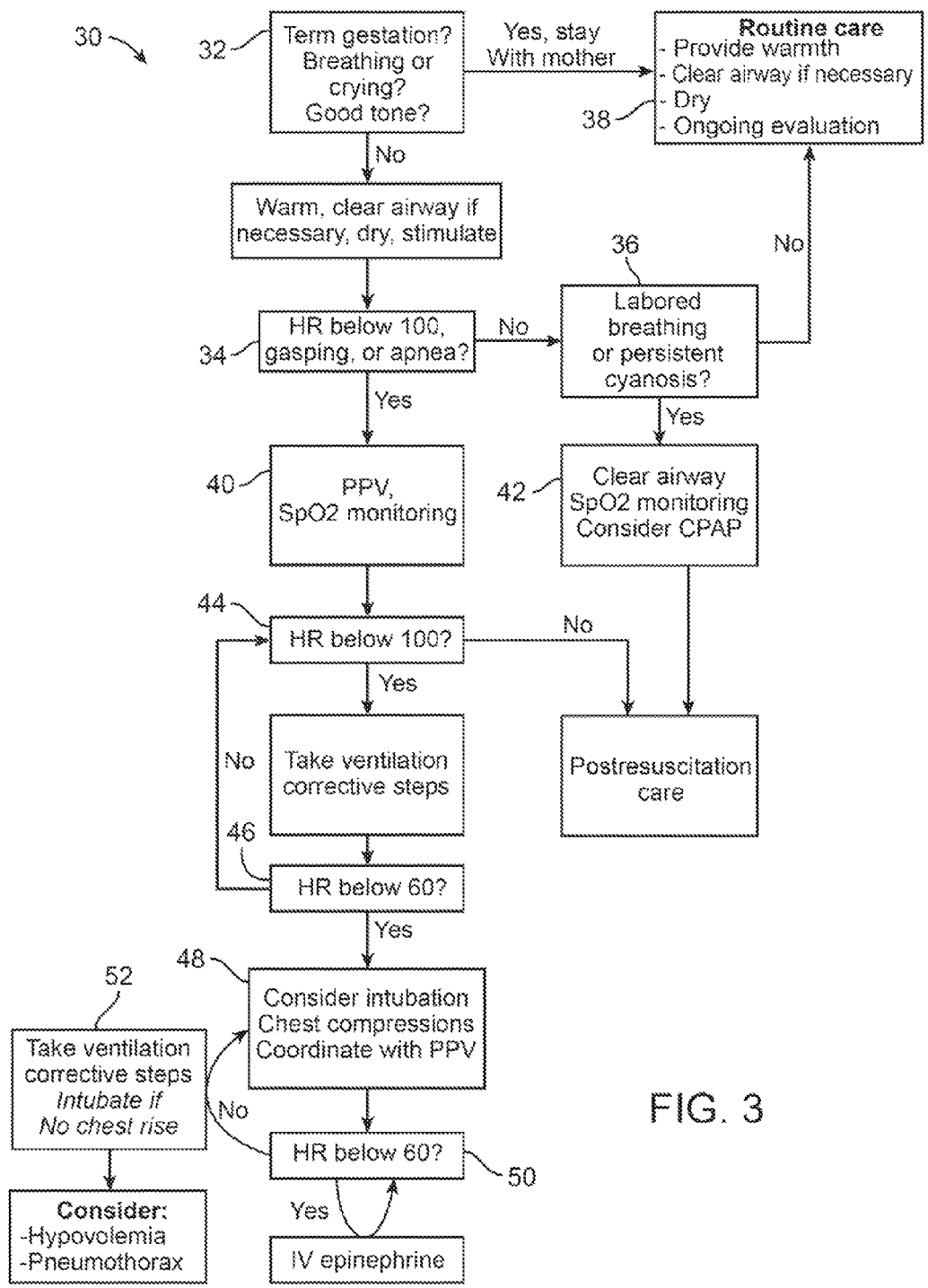
FIG. 3 shows a flow chart illustrating the guidelines for neonatal resuscitation and emergency cardiovascular care provided by the American Heart Association which may be integrated into the neonatal resuscitation system.

In the algorithm of FIG. 3, rather than having the healthcare provider rely on memory alone, the system 10 may automatically prompt and guide the provider with the appropriate measures while following the algorithm. Based on the physiological parameters, as measured by the sensor assembly 18 as well as platform 22 and any other sensors 20, the processor 12 may monitor and record this data in real time to provide accurate information independent of subjective measures prone to human error as well as to provide guidance in prompting the provider to follow the recommended resuscitation algorithm.

Figure 4:
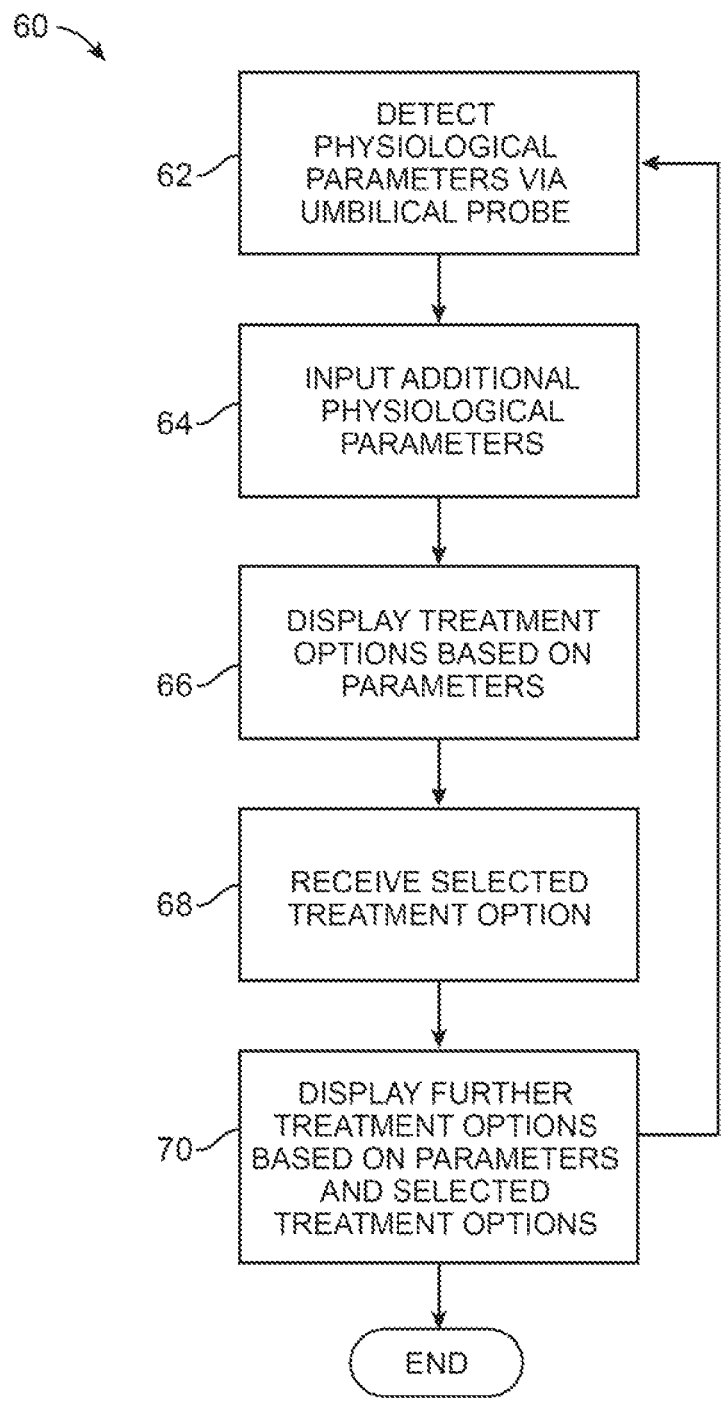
FIG. 4 shows a flow chart illustrating one example of how the neonatal resuscitation system may be utilized.
Figure 6A:
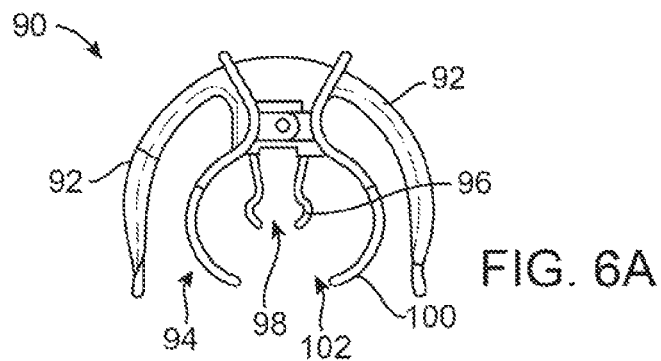
FIGS. 6A to 6D show top, side, and perspective views of one example of a clamping assembly for obtaining physiological parameters from a newborn.
Figure 6B:
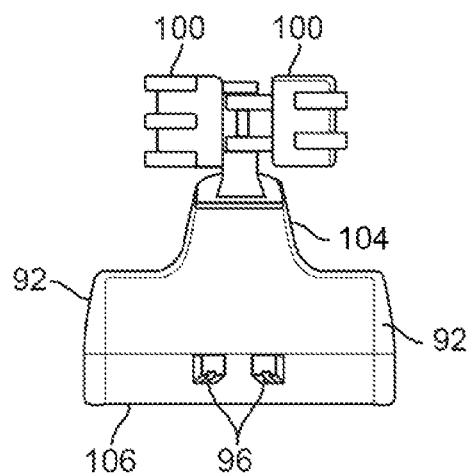
Figure 6C:
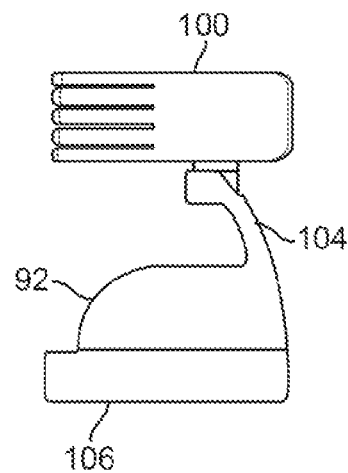
Figure 6D:
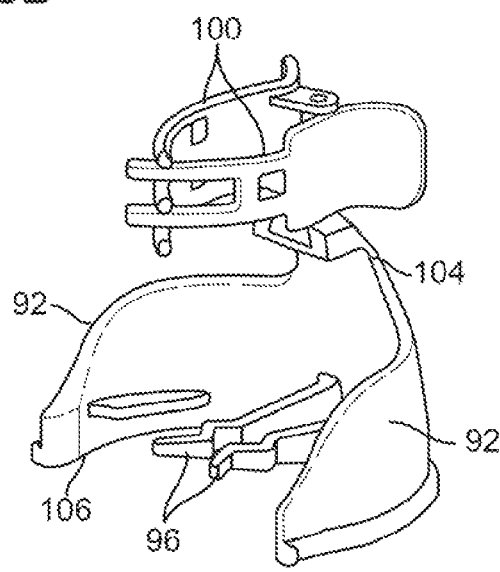

FIG. 4 illustrates another example in the flowchart 60 which shows how the physiological parameters 62 detected via the system 10, such as through the umbilical probe sensor assembly 18, may be integrated with the algorithm of FIG. 3. As illustrated, along with the real time acquisition of the physiological information from the infant NI, the healthcare provider or other member may optionally input additional physiological parameters 64 which may not have been measured by the system 10, e.g., through interface 14 or optional interface 16. The processor 12 may take all the information and accordingly display the appropriate options based on the parameters 66 to the provider through interface 14. The provider may be automatically prompted to take a particular intervention or course of action and/or the provider may be further given the option to receive either the provided treatment option or an alternative treatment option 68 in which case the provider may indicate to the processor 12 through interface 14 and/or 16. Depending upon the selected course of treatment by the provider, the processor 12 may then calculate and display through interface 14 further treatment options based upon the measured (or entered) physiological parameters and/or selected treatment options 70. The treatment and guidance through the algorithm may continue until the infant NI has been successfully resuscitated or until the system 10 has been stopped by the provider or optionally timed out automatically after a passage of time.

The interface 14, as previously mentioned, may function as a touchscreen for receiving input from the healthcare provider. It may also function as a monitor for displaying various data such as real time monitored physiological information as well as recommended treatment options. FIG. 5 shows an example of a user interface 80 which may be displayed on interface 14 showing, e.g., an interface for displaying infant vital signs 82 such as heart rate, oxygen saturation, weight, elapsed time from the start of treatment, etc., which may be displayed numerically or graphically depending upon the desired interface. Interface 14 may also display an interface 84 for prompts and/or alerts which may automatically display to provide guidance and recommendations to the provider for infant treatment. The recommended treatment may, of course, depend upon the physiological data of the infant NI detected by the system 10 as well as the course of treatment provided by the provider and optionally input into the system 10. Additionally, the user interface 80 may also comprise a measurements interface 86 which may display information such as calculated values for drug injections (e.g., epinephrine, etc.) or device sizes (e.g., tubes, etc.) which may be calculated automatically by the processor 12 and displayed on interface 86 depending upon the measured physiological data of the infant as measured by the system 10 or optionally input by the provider. Moreover, user interface 80 may also optionally include a documentation and/or timer interface 88 which may provide an interface for automatically recording not only the real time physiological data of the infant but also any medication and dosages provided as well as the parameters of any other interventional procedures which may have been performed upon the infant.

Although the documentation and/or timer interface 88 may be displayed on a touch screen, they may alternatively include physical buttons as well. Moreover, the interface 88 shown is illustrative of the various features available and may include any number of features, e.g., Start, Stop, Active Respirations, Blow-by, APGAR, PPV, CPAP, Compressions, Intubation, Narcan, Epinephrine, Surfactant, Fluid Bolus, Bicarbonate, UVC, UAC, OG Tube, Peripheral IV, CBG, etc.

To facilitate the interaction with the provider, any touch screen buttons on interface 80 may light when touched and may remain lighted as an indicator that a particular procedure is being performed. For example, the pressing of the "Weigh" button on timer interface 88 may initiate the algorithm and resuscitation timer. Depressing the "PPV" button may trigger a pacing tone at, e.g., 30 beats/second, to guide the provider while the pacing tone may be canceled by depressing the "PPV" button a second time. Depressing the "Compressions" button may also start a pacing tone to guide the provider for chest compressions at, e.g., 90 beats/second, and an illustration of the appropriate position on the infant's chest for compressions may be displayed on the user interface 80 for a period of time, e.g., 5 seconds, as a reminder to the provider.

When prompting or alerting the provider with an alarm or recommended course of treatment, the user interface 80 may incorporate any number of displays. For example, the detected physiological data or prompts may be colored (e.g., red, green, etc. depending upon the status) and/or sized differently from other text on the interface 80.

The user interface 80 is represented as an example of one variation of such an interface which may be displayed upon interface 14. Each of the particular interface features may be modified or omitted entirely depending upon the desired features. However, the user interface 80 is provided as an example of how the various physiological parameters may be detected by the system 10 and displayed to the provider as well as examples of how the interface 14 may also provide guidance and prompting to the provider for accurately guiding the provider through a resuscitation algorithm which is correlated to real time monitored physiological information from the infant.

Because the physiological information and provided procedures may be recorded automatically, the information may be stored in the system 10 for later analysis and/or it may be optionally transmitted to a separate server, such as by encrypted data storage and/or encrypted data transfer, which may accept and store the information. The captured data may be stored for analysis by the healthcare providers at a later time or for access by other parties, e.g., an expert panel of neonatologists. Additionally, the recorded information may also be used for performance feedback to institutions and individual practitioners or optionally for future research for improving neonatal resuscitation.

Another example of how the resuscitation system 10 may be utilized is for use as a training implement for neonatal resuscitation. The processor may be configured to provide a training modality that may optionally utilize a computerized training infant analog which may be interface with the system in real time as a real life infant. The recorded treatment procedures may be optionally used for training neonatal resuscitation and may be used to evaluate and score practitioner competency.

Another example may include the processor in the system 10 being programmed to create and/or send via a wired or wireless protocol (e.g., text messaging, email, cellular protocols, etc.) information to selected individuals. For instance, the system 10 may create a birth announcement with selected information which may be predetermined and/or selected by the birth mother, certain family members, or practitioner where the selected information may include information such as the infant's weight, etc. Such an announcement may be created automatically by the system 10 and/or after the birth by the system 10 and sent via the wired or wireless protocol to the selected individuals either automatically or upon final approval by the birth mother or family member or other approved individual.

Turning now to the sensor assembly, one variation of a clamp assembly 90 which may be temporarily attached to the umbilical cord or umbilical stump US of the infant for sensing and monitoring physiological parameters is shown in the top, side, and perspective views of FIGS. 6A to 6D. Generally, the sensor clamp assembly functions to gather neonatal physiologic data within the first few seconds after birth, as previously mentioned. It also maintains continuous physiologic data capture for at least the first few hours of life and further gathers neonatal physiologic data using multiple sensory modalities without the need for adhesives to adhere to the neonatal skin contact areas.

As described above, the base portion of the sensor clamp assembly may abut the neonatal abdomen and extend a length above the abdomen for attachment to a length of viable umbilical cord prior to cutting of the cord by the delivering physician. Due to the size of the assembly, it may also provide for a standardized length of the umbilical cord to be cut such that a standard predictable length (e.g., for use with umbilical vein or arterial catheters) is provided for future intravascular access by the provider. The clamp site on the umbilical cord is not crushed by the clamping apparatus due to the relatively low pressure applied by the assembly yet the assembly may provide enough clamping force which provides for hemostasis yet maintain blood vessel viability and integrity for future access for cannulation by the pediatrician. The adjustable clamp tension may also allow the practitioner to adjust the position of the clamp on the umbilical cord or stump US. Because the assembly may provide for a standardized protected length of viable umbilical stump US, the assembly may provide for a one-size-fits-all length of catheter. Moreover, because the clamp assembly is adjustable, it may hold the sensors integrated along the assembly in a fixed position relative to the umbilical cord or stump without the need for adhesives.

In the particular variation shown, the clamp assembly 90 may generally comprise a pair of stabilizing members 92 which form a contact surface 106 for optional placement against the skin surface of the infant NI surrounding the umbilical stump US. The stabilizing members 92 are shown as curved or arcuate members which extend into apposition relative to one another to form an opening 94 for receiving the umbilical stump US and/or umbilical cord, e.g., forming a diameter of 0.5 to 4 cm, although the diameter may be formed to be lower or greater depending upon the desired size. A pair of first stabilizing arms 96 may protrude into the opening 94 from between the stabilizing members 92 and form a receiving channel 98 such that each of the first stabilizing arms 96 are adjustable relative to one another and biased towards one another to temporarily clamp over or onto a portion of the umbilical stump US. The first stabilizing arms 96 may be positioned relatively closer towards the contact surface 106.

A second pair of stabilizing arms 100 may be positioned in proximity to the first stabilizing arms 96 such that a receiving channel 102 defined by the second stabilizing arms 100 is aligned collinearly with the receiving channel 98 formed by the first stabilizing arms 96. Moreover, the second stabilizing arms 100 may be positioned upon an adjustable neck 104 which allows for the relative adjustment between the first and second stabilizing arms 96, 100. In use, while the first stabilizing arms 96 may hold onto the umbilical stump US to maintain its position, the second stabilizing arms 100 may also clamp temporarily onto an upper portion of the umbilical stump US or upon a portion of the umbilical cord such that the umbilical stump US is maintained in a secure configuration relative to the infant's body.

In yet another alternative, the second stabilizing arms 100 may be separated from the first stabilizing arms 96 and removed from the assembly leaving the first stabilizing arms 96 clamped upon the umbilical stump US to provide hemostasis.

As described in further detail below, a number of different types of sensors may be integrated into the clamp assembly 90, e.g., within the first or second stabilizing arms 96, 100, along the stabilizing members 92 (such as a sensor "puck" insertable into the base), or in other locations along the clamp assembly 90 in proximity or in contact with the umbilical stump US. In one example, one or more sensors along the clamp assembly 90 may comprise piezoelectric sensors in contact with the umbilical stump US for detecting the infant heart rate. Additionally, one or more electrocardiogram (ECG) sensors may also be integrated as well as one or more infrared sensors for pulse oximetry.

Attaching the clamp assembly 90 to the umbilical stump US and detecting an infant's heart rate can potentially be performed, e.g., in less than 10 seconds, whereas detection of an infant's pulse would usually otherwise take more than 60 to 70 seconds. Moreover, because the infant's heart rate is measured directly from the blood vessels remaining within umbilical stump US (and/or skin and abdominal wall), the measurement is objective and not limited to subjective manual heart rate detection by a medical practitioner. Additionally, because the clamp assembly 90 may remain secured to the umbilical stump US for the duration of the resuscitation (or even afterwards), the sensor may provide a continuous data stream of neonatal heart rate throughout resuscitation and/or during neonatal I.C.U. or neonatal nursery stay.

Additionally, the ECG sensors (e.g., silver-silver chloride conductance pads or any other conductance type pads) integrated into the clamp assembly 90 may also detect and monitor the infant's ECG waveforms throughout the resuscitation procedure to also provide the ability for real time monitoring and analysis of cardiac waveform and rhythm analysis as well as providing the opportunity for earlier heart rate and rhythm analysis for interventions not previously included in conventional neonatal resuscitation algorithms. The assembly 90 may also optionally provide sensors for transthoracic impedance plethysmography sensing for neonatal blood flow analysis. The assembly 90 may further provide, e.g., transcutaneous capillary pH analysis, transcutaneous capnometry analysis, transcutaneous capillary blood glucose levels, non-contact pulse oximetry, CMOS-based digital imaging, radio-frequency sensors, piezoelectric sensors, etc.

The assembly 90 may also hold the umbilical cord or stump US relatively upright relative to the infant abdomen and taut between the first or second stabilizing arms 96, 100 to facilitate intravascular access and may be secured to the infant utilizing a single hand of the provider.

Another variation of the sensor assembly is shown in the side and top views of FIGS. 7A and 7B, which illustrate a clamp assembly 110 secured to a portion of an umbilical stump US. In this variation, the assembly 110 may generally comprise a first securement member 112 which may be secured to a second securement member 132 positioned in apposition around, across, or adjacent to the umbilical cord UC or stump US. Wires 122 attached to one or both of the members 112, 132 may electrically couple the assembly 110 to the processor 12. The assembly 110 may incorporate any of the various sensors described herein although the example illustrated shows a first ECG lead 114 positioned along first securement member 112 and a second ECG lead 126 positioned along second securement member 132 such that when the members 112, 132 are secured to the umbilical stump US the ECG leads 114, 126 are aligned in apposition to one another across the umbilical stump US thus allowing for the leads 114, 126 to detect the signals across the stump US. Also illustrated is a light emitting diode (LED) 116 positioned along second member 132 and photodiode 124 positioned along first member 112 in apposition relative to one another such that the emitted light from LED 116 may be transmitted into a portion of the skin along the umbilical stump US and detected by the corresponding photodiode 124. In the event that light reflectance is used to detect the signals rather than light transmission entirely through the stump US, the securement members 112, 132 may be secured across or adjacent to the stump US such that the light source may be positioned adjacent to the photodetector to receive reflected light from the stump US rather than transmitted light.

Although described with the use of wired communications, the detected and sensed information may alternatively be transmitted using various wireless communications protocols such as those described above, e.g., BLUETOOTH®, WiFi, radio frequency, microwave, cellular protocols, etc.

To facilitate placement and alignment of the members 112, 132 relative to the umbilical stump US, one or more optional external indicators or markers 118 may be positioned along the members 112, 132 to aid with aligning the integrated sensors with the umbilical stump US. Additionally, one or both members 112, 132 may also optionally include temperature sensor 120 along a portion of the assembly 110 which contacts the abdominal skin surface of the infant.

Because the size of the umbilical cord UC and/or umbilical stump US may vary between infants, the assembly 110 may have its first securement member 112 made from a flexible layer 138 and second securement member 132 also made from a flexible layer 134 which may each have a respective adhering layer 140 and 136, as shown in the top view of FIG. 8A, which is positioned to be in apposition relative to one another. Each of the adhering layers 136, 140 may be made from a gelatinous adhesive that may adhere at least temporarily not only to one another but also around the umbilical stump US. With the flexibility of the members 112, 132, the assembly 110 may define a conforming region 130 which can vary in size to accommodate variably-sized umbilical stumps 142, as shown in FIG. 8B, while the members 112, 132 adhere to one another along contact regions 128 on either or both sides of the umbilical stump US with a relatively low compressive force exerted onto the umbilical stump US. In this manner, each of the sensors may remain in contact against the surface of the umbilical stump US for sensing. Moreover, the assembly 110 may be repositioned and/or removed from the umbilical stump US once resuscitation has been completed or until a later time.

Figure 9:
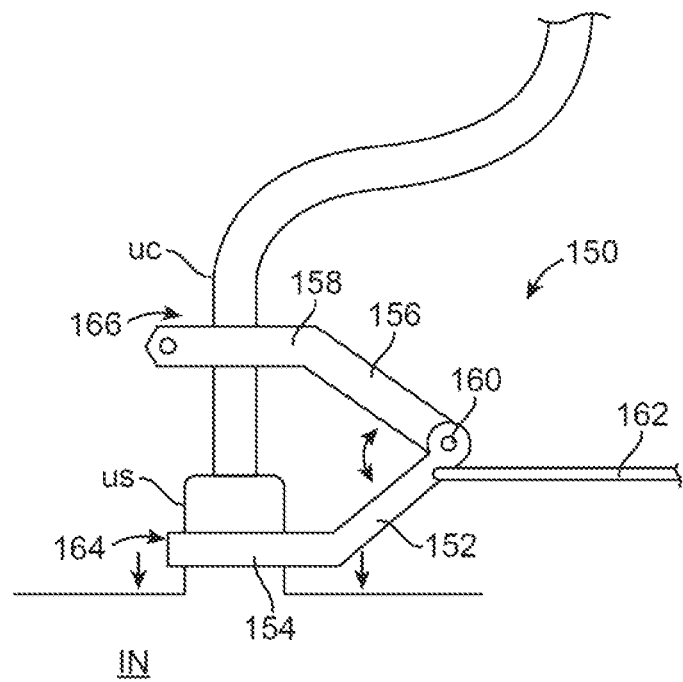
FIG. 9 shows a side view of another variation illustrating a clamping assembly which may be biased to tension the umbilical cord and stump relative to one another to provide for a secure connection.

FIG. 9 shows a side view of another variation in which a clamp assembly 150 may generally comprise a clamping structure having, e.g., a biasing mechanism to maintain probe position and contact against the skin of the infant IN. As shown, the clamping assembly 150 may have a first support member 152 extending to a first clamping member 154 which defines a first receiving channel 164 for temporarily clamping onto a portion of the umbilical stump US. First support member 152 and first clamping member 154 may be optionally angled relative to one another to facilitate positioning of the first clamping member 154 against the umbilical stump US. Similarly, second support member 156 may extend at an angle relative to first support member 152 with second clamping member 158 extending optionally at an angle relative to the second support member 156. A second receiving channel 166 may be defined at a distal end of the second clamping member 158 for securement onto a distal portion of the umbilical stump US or along a portion of the umbilical cord UC, as shown. One or more wires 162 may electrically couple the integrated sensors positioned within one or both of the receiving channels 164, 166 of the assembly 150 to the processor 12.

The first and second support members 152, 156 may be pivotably coupled to one another in a biased connection 160, e.g., in an articulated spring-loaded coupling, which may urge the members 152, 156 away from one another, as indicated by the arrow. With the first clamping member 154 secured to the umbilical stump US and against the abdominal skin of the infant IN and with second clamping member 158 secured to an upper portion of either the umbilical stump US or umbilical cord UC, e.g., about 3 cm away from first clamping member 154, the assembly 150 may be securely held in position relative to the infant IN to maintain the sensors in contact with the infant IN, umbilical stump US, and/or umbilical cord UC. Additionally, because of the biasing force from the connection 160, the umbilical stump US and/or umbilical cord UC may be maintained in a straightened configuration relative to the abdomen of the infant IN allow for intravascular access.

Figure 10:
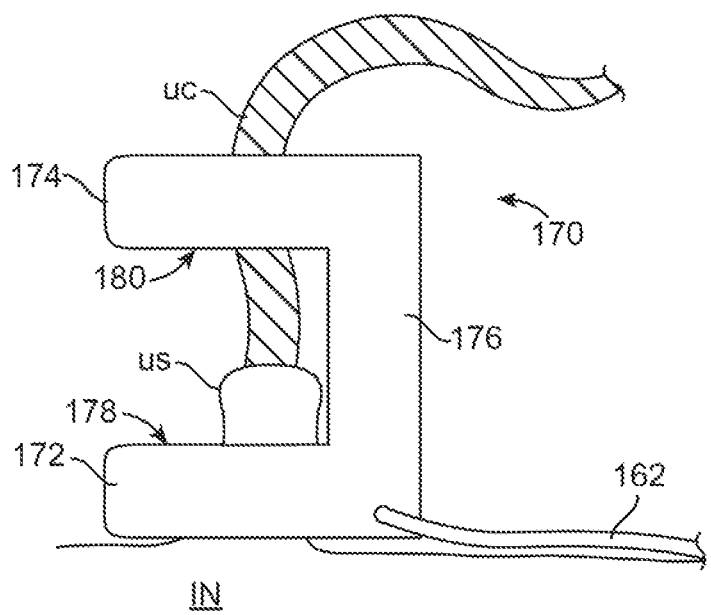
FIG. 10 shows a side view of another variation of a clamping assembly utilizing a secure bridging member.

Yet another variation is shown in the side view of FIG. 10 which illustrates clamp assembly 170 which may be comprised generally of a first support member 172 which defines a first receiving channel 178 for receiving the umbilical stump US and a second support member 174 which defines a second receiving channel 180 for receiving an upper portion of the umbilical stump US or umbilical cord UC. The support members 172, 174 may be attached to one another via a bridging member 176 which may adjust a height between the members 172, 174. Optionally, the second support member 174 may be separated from the first support member 172 and removed from the assembly leaving the support member 172 clamped upon the umbilical stump US to provide hemostasis. The remaining portion of the clamped umbilical cord UC may be left flaccid to lie against the abdominal wall after the need for resuscitation has passed.

The assembly 170 as well as each of the other variations shown and described herein may incorporate any number of the sensors within the assemblies for detecting and monitoring the physiological parameters of the infant from the umbilical cord UC and/or umbilical stump US. Moreover, each of the assemblies may be adjustable to vary the height between the securement members as desired or necessary. Furthermore, the surface of the clamping members in any of the variations herein may be optionally roughened or they may integrate projections or protrusions to inhibit slippage between the umbilical tissue and the assembly.

Figure 11A:
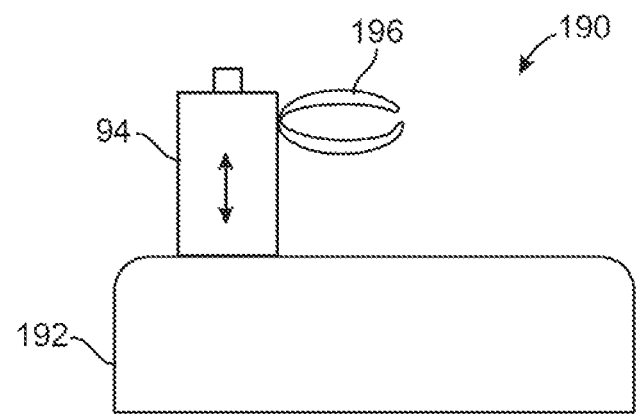
FIGS. 11A and 11B show side views of another variation of a clamping assembly having an adjustable bridging member.
Figure 11B:
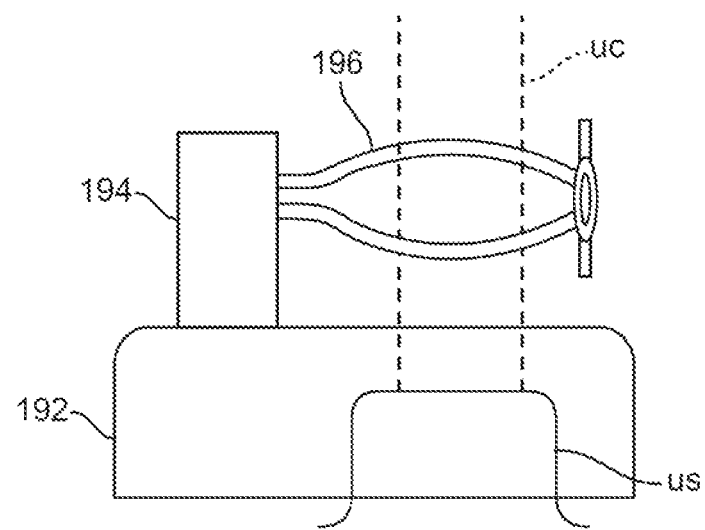

Yet another variation is shown in the side view of FIGS. 11A and 11B, which illustrate a clamp assembly 190 having a base 192 which defines an opening for receiving the umbilical stump US. The bridging member 194 may extend from the base 192 and have an adjustable clamp members 196 extending from the base such that the opening of the clamp members 196 is aligned with the opening through the base 192 for holding the umbilical cord UC and/or umbilical stump US. The clamp members 196 may be adjustably positioned along the bridging member 194 to vary its height relative to base 192, as desired. The one or more sensors may be housed within the base 192 for contact with the umbilical stump US.

Figure 12:
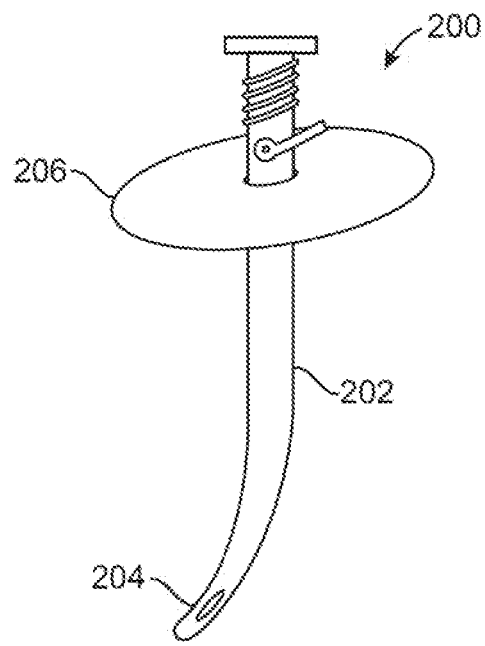
FIG. 12 shows a side view of an umbilical vein catheter which may be inserted into the umbilical cord or stump.

With the clamping assembly maintaining a secure configuration of the umbilical stump US or cord UC, the assembly presents an entry point for an umbilical vein catheter (UVC) 200 which may be utilized with the clamping assembly for gaining intravascular access to the infants vascular system via the umbilical stump US or cord UC. As shown in the side view of FIG. 12, an example of a UVC 200 is illustrated as having a catheter length 202 with a tapered tip 204 and an adjustable dial 206.

Figure 13:
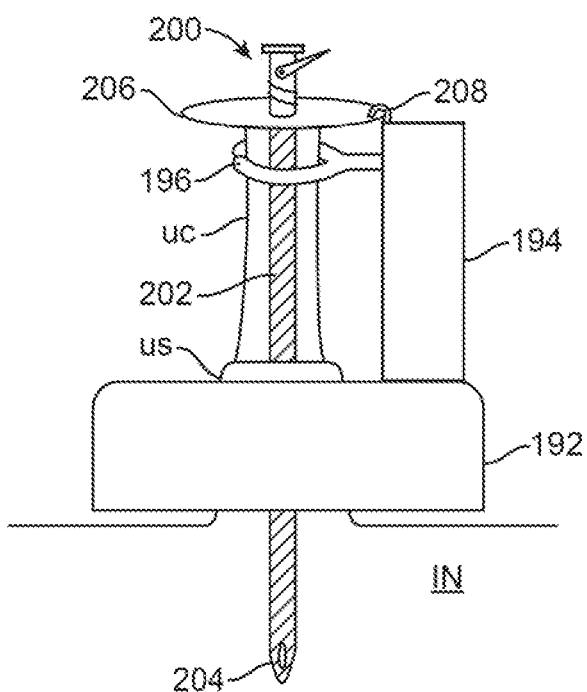
FIG. 13 shows a side view of an umbilical vein catheter integrated with a clamping assembly.

In use, the UVC 200 may be inserted into the umbilical cord UC or stump US with a proximal portion of the catheter 200 secured to the clamp members 196, as shown in the side view of FIG. 13. The adjustable dial 206 may be further secured to the assembly 190 via a lock 208 which may attach the dial 206 to a portion of bridging member 194. Once the UVC 200 has been inserted into the umbilical stump US and locked to assembly 190, dial 206 may be rotated to adjust a depth of the tip 204 relative to the assembly 190 and umbilical stump US. For example, dial 206 may be rotated until the tip 204 is at a depth of, e.g., about 2 cm, below the abdominal wall in the umbilical vein.

Umbilical vessel catheterization usually is usually performed 5 to 10 minutes into a resuscitation attempt and typically requires 5 to 15 minutes of practitioner time to properly place and secure in position the UVC. However, utilizing the clamping assembly, the UVC 200 may be placed within the umbilical vessel within, e.g., the first 30 seconds of a resuscitation and may require less than one minute of practitioner time. The use of UVC 200 may be integrated with any of the assemblies described herein as desired or as practicable.

The applications of the devices and methods discussed above are not limited to the securement of umbilical cords and stumps but may include any number of further treatment applications. Moreover, such devices and methods may be applied to other treatment sites within the body. Modification of the above-described assemblies and methods for carrying out the invention, combinations between different variations as practicable, and variations of aspects of the invention that are obvious to those of skill in the art are intended to be within the scope of the claims.

What is claimed is:

1. A method for treating a neonatal infant, comprising:
providing a processor having a user interface;
securing an umbilical probe sensing assembly to tissue of an umbilical stump and/or cord of the infant such that one or more sensors integrated within the assembly contact the tissue and wherein the assembly is removably securable to the umbilical stump and/or cord;
detecting one or more physiological parameters from the infant via the one or more sensors wherein the parameters are sent to the processor;
providing a recommended course of treatment to a healthcare provider via the user interface, wherein the course of treatment is changed when the infant is determined to be distressed based upon one or more physiological parameters detected by the sensors.

2. The method of claim 1 wherein securing comprises placing a base of the assembly into contact against a skin surface adjacent to the umbilical stump.

3. The method of claim 1 wherein securing comprises securing the assembly into contact with the umbilical stump upon birth of the infant.

4. The method of claim 1 wherein securing comprises securing one or more securement members onto a first portion of the umbilical stump.

5. The method of claim 4 further comprising securing a second portion of the umbilical stump or cord with additional securement members such that a length of the umbilical stump or cord between the first and second portions is taut.

6. The method of claim 1 wherein securing comprises inhibiting necrosis of the umbilical stump by securing the assembly at a clamping pressure below a crushing pressure sufficient to cause necrosis.

7. The method of claim 1 wherein detecting one or more physiological parameters comprises detecting a heart rate, ECG waveform, oxygen saturation, weight, or carbon dioxide level of the infant.

8. The method of claim 1 wherein detecting further comprises detecting additional physiological parameters via additional sensors separate from the assembly.

9. The method of claim 1 further comprising prompting the user with the changed course of treatment via an alarm on the interface.

10. The method of claim 1 further comprising securing an umbilical vein catheter to the assembly.

11. The method of claim 1 wherein determining whether the infant is distressed comprises detecting via the one or more sensors whether at heart rate of the infant is below 100 beats per minute.

12. The method of claim 11 further comprising determining whether breathing of the infant is labored via an oxygen saturation level detected by the one or more sensors.

13. The method of claim 12 wherein the changed course of treatment comprises prompting the user to provide positive pressure ventilation via the interface.

14. The method of claim 13 further comprising further detecting via the one or more sensors whether the heart rate of the infant is below 60 beats per minute.

15. The method of claim 14 wherein the changed course of treatment comprises prompting the user to provide intubation to the infant.

16. The method of claim 15 further comprising calculating and displaying a size of an intubation tube for the infant via the processor.

17. The method of claim 14 wherein the changed course of treatment comprises coordinating chest compressions via the interface.

18. The method of claim 1 further comprising calculating and displaying a dosage of a drug via the processor for administration to the infant based upon a detected weight of the infant.

19. The method of claim 17 wherein coordinating chest compressions comprises providing a metronome.

20. The method of claim 13 wherein prompting comprises providing a metronome.

21. The method of claim 1 wherein the course of treatment is changed when the infant is determined to be improving based upon one or more physiological parameters detected by the sensors.

* * * * *